Figure 1:
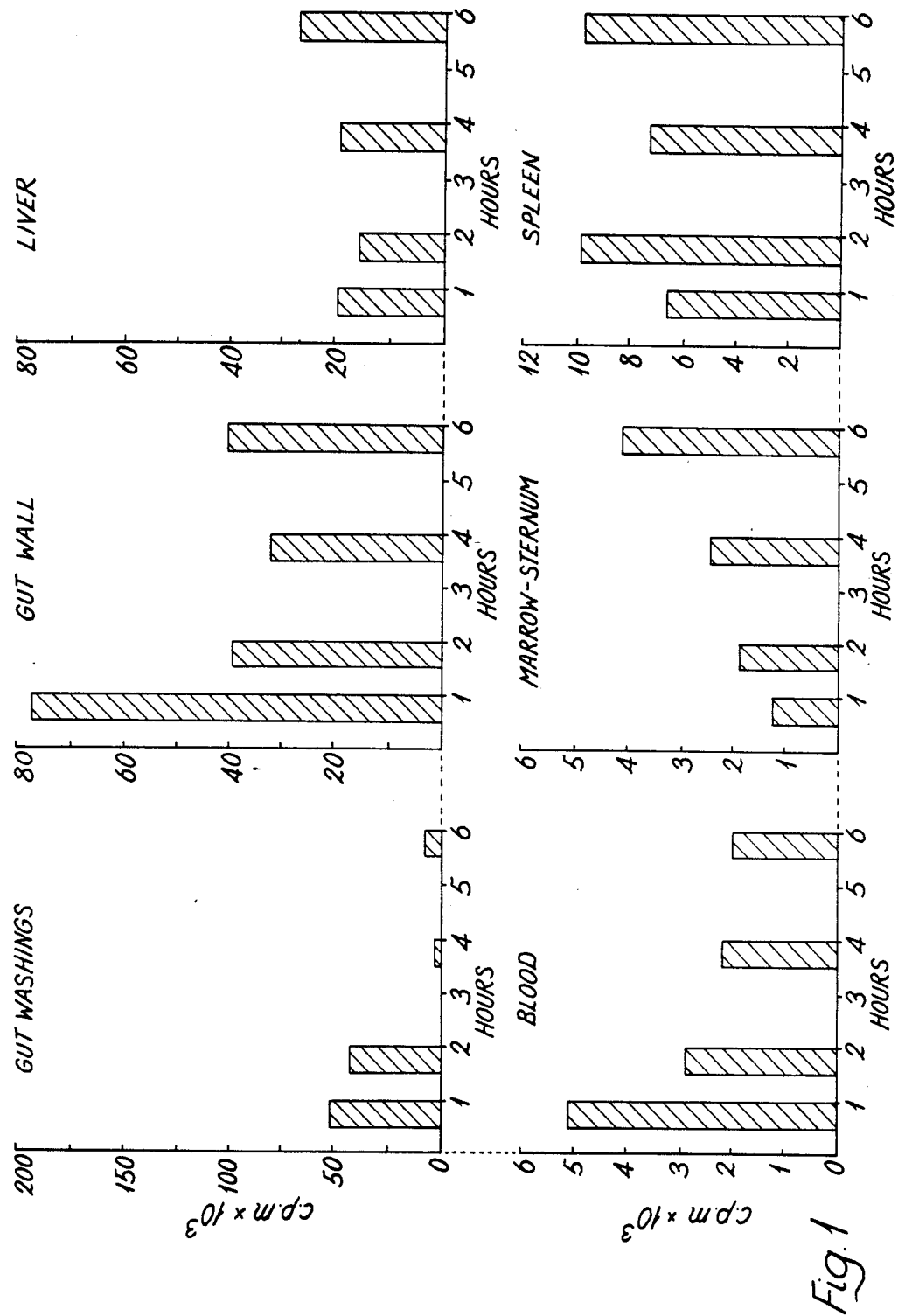

United States Patent [19]

Hider et al.

[11] Patent Number: 4,575,502

[45] Date of Patent: Mar. 11, 1986

[54] PHARMACEUTICAL COMPOSITIONS

[75] Inventors: Robert C. Hider, Clacton; George Kontoghiorghes, London; Michael A. Stockham, Saffron Walden, all of England

[73] Assignee: National Research Development Corporation, London, England

[21] Appl. No.: 542,976

[22] Filed: Oct. 18, 1983

[30] Foreign Application Priority Data

Oct. 22, 1982 [GB] United Kingdom ................. 8230150

[51] Int. Cl.⁴ ............................................ A61K 31/555
[52] U.S. Cl. .................................... 514/184; 514/814
[58] Field of Search ........................................ 424/245

[56] References Cited

U.S. PATENT DOCUMENTS

| | | | |
|---|---|---|---|
| 2,865,938 | 12/1958 | Rosenfelder | 424/245 |
| 2,904,573 | 9/1959 | Oroshnik et al. | 424/245 |
| 4,018,907 | 4/1977 | Scarpellino | 426/250 |
| 4,018,934 | 4/1977 | Parliment | 426/250 |

FOREIGN PATENT DOCUMENTS

| | | |
|---|---|---|
| 2613500 | 10/1976 | Fed. Rep. of Germany . |
| 2130M | 4/1965 | France . |
| 1377006 | 12/1974 | United Kingdom . |

OTHER PUBLICATIONS

J. Chem. Research, (M), 1980, paper F/016/80, 3919–3927.
Chem. Phar. Bull., 28(9) 2570–2579 (Kimura et al.).
Product Bulletins for Ethyl Maltol and Maltol, Trade Names "Veltrol-Plus" and Veltrol.
Pfizer Chemical Europe & Africa, Basic Data Sheet No. 865, "Veltol"; Basic Data Sheet 867 Veltol–Plus.
Pfizer Chemicals Produits Chimiques Chemikalien, Technical Bulletin, 04/A/Mar. 1974, "Veltol"; Veltol–Plus.
Chemical Abstracts, vol. 94, 1981, 41144j.
Chemical Abstracts, vol. 75, 1971, 115362k.
Chemical Abstracts, vol. 94, 1981, 24201h.
Kanasagabai Ganeshaguru, Biochemical Pharmacology, 29, 1980, 1275.
R. W. Grady, et al., Journal of Pharmacology and Experimental Therapeutics, 1976, 196, 478, 146.
White et al., "British Journal of Haematology, 33, 1976, pp. 487–495.
Foye et al., Journal of Pharmaceutical Sciences, 61, 1972, 1204.
Stefanovic, A., et al., Collection of Czechoslovakian Chemical Communications, 33, Feb. 5, 1968, pp. 4198–4214.
Hugh A. Akers et al., Journal of Bacteriology, Jan., 1980, pp. 164–168.
T. H. Bothwell, et al., American Journal of Clinical Nutrition, Jan., 1964, pp. 47–51.
Jacob J. Habeeb, et al., Journal of Coordination Chemistry, 1978, pp. 8, 27.
Gerard, Christian, et al., J. Chem. Research, 1980, 314.
Y. Kidani, Nagoya Shiritsu Daigaku Yakugakubu Kenkyu Nempo, 18, 1970, 16–21.
Chemical Abstracts, vol. 84, 1976, Columbus, Ohio, USA, p. 19.

Primary Examiner—Frederick E. Waddell
Attorney, Agent, or Firm—Oblon, Fisher, Spivak, McClelland & Maier

[57] ABSTRACT

Pharmaceutical compositions containing an iron complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms are of value for the treatment of iron deficiency anaemia.

13 Claims, 7 Drawing Figures

PHARMACEUTICAL COMPOSITIONS

This invention relates to iron compounds for use in pharmaceutical compositions for the treatment of iron deficiency anaemia.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born, particularly in certain animal species such as the pig. Moreover, in certain pathological conditions there is a mal distribution of body iron leading to a state of chronic anaemia. This is seen in chronic diseases such as rheumatoid arthritis, certain haemolytic diseases and cancer.

Although a wide range of iron compounds is already marketed for the treatment of iron deficiency anaemia, the level of iron uptake by the body from these compounds is often quite low thereby necessitating the administration of relatively high dosage levels of the compound. The administration of high dose, poorly absorbed, iron complexes may cause siderosis of the gut wall and a variety of side effects such as nausea, vomiting, constipation and heavy malodorous stools.

The present invention relates to a group of iron complexes which we have identified as being of particular value for use at relatively low dosage levels in the treatment of iron deficiency anaemia. The hitherto unrecognised value of these complexes in such a content, as shown by in vivo experiments, is unexpected in view of the well known need for improved iron compounds for the treatment of iron deficiency anaemia. This is particularly so as among the compounds whose iron complexes are of the most interest for use in pharmaceutical compositions according to the present invention is a significant number of compounds which are naturally occurring materials, or are readily derivable from such materials, and which have been known for some time to be capable of forming iron complexes. Furthermore, several of these compounds have previously been used in foodstuffs thereby indicating their nontoxic nature and the consequent suitability for pharmaceutical use of their iron complexes.

According to the present invention a pharmaceutical composition comprises an iron complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, together with a physiologically acceptable diluent or carrier.

The iron complexes present in the pharmaceutical compositions according to the present invention preferably contain iron in the ferric state. Although the use of complexes containing iron in the ferrous state may be considered, such complexes tend to be less stable and are thus of less interest. The iron complexes are preferably neutral and this is conveniently achieved by complexing with the iron cation the appropriate number of anions derived from the hydroxypyrone (through the conversion OH→O−) necessary to produce neutrality. Preferred iron complexes of use in the present invention are thus of the 3:1 form, containing three hydroxypyrone anions complexed with a ferric cation.

The substituted 3-hydroxy-4-pyrones may carry more than one type of aliphatic hydrocarbon group but this is not usual and, indeed, substitution by one rather than two or three aliphatic hydrocarbon groups is preferred. The aliphatic hydrocarbon groups may be cyclic or acyclic, having a branched chain or especially a straight chain in the latter case, and may be unsaturated or especially saturated. Groups of from 1 to 4 carbon atoms and particularly of 1 to 3 carbon atoms are of most interest. Alkyl groups are preferred, for example cyclic groups such as cyclopropyl and especially cyclohexyl but, more particularly preferred are acyclic alkyl groups such as n-propyl and isopropyl, and especially ethyl and methyl. Substitution at the 2- or 6-position is of especial interest although, when the ring is substituted by the larger aliphatic hydrocarbon groups, there may be an advantage in avoiding substitution on a carbon atom alpha to the

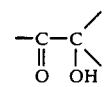

system. This system is involved in the complexing with iron and the close proximity of one of the larger aliphatic hydrocarbon groups may lead to steric effects which inhibit complex formation.

Examples of specific compounds whose iron complexes may be used in compositions according to the present invention are shown by the following formulae (I), (II) and (III);

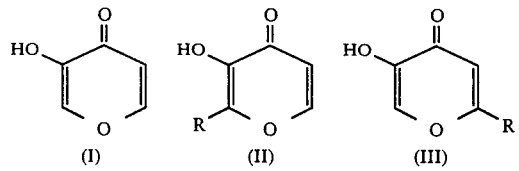

in which R is an alkyl group, for example methyl, ethyl, n-propyl or isopropyl. Among these compounds 3-hydroxy-2-methyl-4-pyrone (maltol; II, R=CH$_3$) is of most interest, whilst 3-hydroxy-4-pyrone (pyromeconic acid; I), 3-hydroxy-6-methyl-4-pyrone (isomaltol; III, R=CH$_3$) and particularly 2-ethyl-3-hydroxy-4-pyrone (ethylpyromeconic acid; II, R=C$_2$H$_5$) are also of especial interest.

In the case of certain of the hydroxypyrones referred to above, for example maltol, ethylpyromeconic acid and isomaltol, the formation of an iron complex of the compound has been referred to in the literature, although its should be noted that the procedures described in the literature for the production of such complexes often would not provide complexes of a form which is preferred for use in the pharmaceutical compositions according to the present invention. In the case of the other hydroxypyrones, the iron complexes are novel and are included, per se, by the present invention.

The iron complexes are conveniently prepared by the reaction of the hydroxypyrone and iron ions, the latter conveniently being derived from an iron salt, particularly a ferric halide and especially ferric chloride. The reaction is conveniently effected in a suitable mutual solvent and water may often be used for this purpose. If desired, however, an aqueous/organic solvent mixture may be used or an organic solvent, for example ethanol, methanol or chloroform and mixtures of these solvents together and/or with water where appropriate. In particular, methanol or especially ethanol may be used where it is desired to effect the separation of at least a major part of a by-product such as sodium chloride by precipitation whilst the iron complex is retained in solution.

It should be appreciated that the nature of the iron complex obtained by the reaction of a hydroxypyrone and iron ions will depend both on the proportion of these two reactants and upon the pH of the reaction medium. Thus, for the preparation of the 3:1 ferric complex, for example, the hydroxypyrone and the ferric salt are conveniently mixed in solution in a 3:1 molar proportion and the pH adjusted to a value in the range of 6 to 9, for example 7 or 8. If a similar excess of hydroxypyrone:iron is employed but no adjustment is made of the acidic pH which results on the admixture of the hydroxypyrone and an iron salt such as ferric chloride, then a mixture of the 2:1 and 1:1 complex will instead be obtained.

Reaction to form the iron complex is generally rapid and will usually have proceeded substantially to completion after 5 minutes at about 20° C., although a longer reaction time may be used if necessary. Following separation of any precipitated by-product, such as a sodium chloride in the case of certain solvent systems, the reaction mixture may conveniently be evaporated on a rotary evaporator or freeze dried to yield the solid iron complex. This may, if desired, be crystallised from a suitable solvent, for example water, an alcohol such as ethanol, or a solvent mixture, including mixtures containing an ether. The present invention further includes a process for the preparation of an iron complex of 3-hydroxy-4-pyrone or of a 3-hydroxy-4-pyrone in which a hydrogen atom attached to one or more ring carbon atoms is replaced by an aliphatic hydrocarbon group of 1 to 6 carbon atoms, which comprises reacting said hydroxypyrone with iron ions and isolating the resultant complex; such a process being restricted, however, to exclude processes for the preparation of those particular forms of iron complex of particular hydroxypyrones which have already been described in the literature.

Whilst for some uses it may be appropriate to prepare the iron complex in substantially pure form, i.e. substantially free from by-products of manufacture, in other cases, for example with a solid oral formulation as described hereinafter, the presence of by-products such as sodium chloride may be quite acceptable. In general, however, the neutral 3:1 [hydroxypyrone:iron (III)] complex is of particular interest in a form which is substantially free at least from those by-products which are complexes containing difference proportions of hydroxypyrone and iron, in particular the 2:1 and 1:1 complexes. Accordingly the present invention includes an iron complex, for example the 3:1 hydroxypyrone:iron (III) complex, of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, but excluding 3-hydroxy-2-methyl-4-pyrone, when in a form substantially free from iron complexes of the pyrone containing other proportions of iron. As indicated hereinafter, it may be advantageous under some circumstances for the iron complex to be used in admixture with the free pyrone. It is possible to produce such a mixture by mixing the two components either in the solid form or in solution, followed by isolation of a solid mixture in the latter case when a solid composition is required. However, it may be more convenient to obtain such a mixture by reacting a molar proportion of the pyrone and iron ions of greater than 3:1. It should be stressed, however, that the conditions as well as the proportion of reactants used in the reaction are of importance if a mixture of the free pyrone and the preferred neutral 3:1 complex is to be obtained. In particular, as indicated previously, the pH of the reaction mixture is particularly important and, because of this fact, certain prior art procedures concerned with the use of iron pyrone complexes in food colouring, for example as described in U.S. Pat. No. 4,018,907, substantially fail to yield the 3:1 complex even though an excess of the pyrone is present, owing to the lack of pH control.

Certain hydroxypyrones, such as maltol, are available commercially.

With others, a convenient starting material in many instances consists of pyromeconic acid which is readily obtainable by the decarboxylation of meconic acid. Thus, for example, pyromeconic acid may be reacted with an aldehyde to insert a 1-hydroxyalkyl group at the 2-position, which group may then be reduced to produce a 2-alkyl-3-hydroxy-4-pyrone. The preparation of 2-ethyl-3-hydroxy-4-pyrone, etc, by this route is described in U.S. application Ser. No. 310,141 (series of 1960).

It will be appreciated that these are not the only routes available to these compounds and their iron complexes and that various alternatives may be used as will be apparent to those skilled in the art.

The iron complexes may be formulated for use as pharmaceuticals for veterinary or human use by a variety of methods. For instance, they may be applied as an aqueous, oily or emulsified composition incorporating a liquid diluent, which composition most usually will be employed for parenteral administration and therefore may conveniently be sterile and pyrogen free. Oral administration is, however, generally to be preferred for the treatment of iron deficiency anaemia in humans and the complexes of the present invention may be given by such a route. Although compositions incorporating a liquid diluent may be used for oral administration, it is preferred to use compositions incorporating a solid carrier, for example a conventional solid carrier material such as starch, lactose, dextrin or magnesium stearate. The iron complex will of course be present in such a preferred composition in solid form, which form is accordingly a preferred one for the complex, and such a solid composition may conveniently be presented in tablet form.

In the case of animals, compositions for parenteral administration are of greater interest than with humans. The problems of iron deficiency anaemia in newly born pigs arise primarily during the first three weeks or so of their life when a very rapid weight gain takes place. The iron complexes of the present invention may be used to treat piglets directly by a parenteral route but an alternative approach is to enhance the iron content of the milk on which the piglets are feeding by treating the mother pig using oral or parenteral administration, for example an injectable slow release preparation.

Other forms of administration than by injection or through the oral route may also be considered in both human and veterinary contexts, for example the use of suppositories for human administration.

Compositions may be formulated in unit dosage form, i.e. in the form of discrete portions containing a unit dose, or a multiple or sub-unit dose. Whilst the dosage of hydroxypyrone iron complex given will depend on various factors, including the particular compound which is employed in the composition, it may be stated by way of guidance that maintenance at a satisfactory level of the amount of iron present in the human body will often be achieved using a daily dosage, in terms of the iron content of the compound, which lies in a range from about 0.1 to 100 mg and often in a range from 0.5 to 10 mg, for example 1 or 2 mg, veterinary doses being on a similar g/Kg body weight ratio. However, it will be appreciated that it may be appropriate under certain circumstances to give daily dosages either below or above these levels. In general, the aim should be to provide the amount of iron required by the patient without administering any undue excess and the properties of the pharmaceutical compositions according to the present invention are particularly suited to the achievement of this aim. Similarly, the concentration of iron in the pharmaceutical composition in the form of the hydroxypyrone complex may vary quite widely, for example over a range from about 0.001 to about 20% w/w. However, it is more usual for the concentration to exceed 0.01% w/w and it may often exceed 0.05 or 0.1% w/w, whilst a more usual limit for the upper end of the range is about 13% w/w. A common range of concentration is 0.05 to 5% w/w, for example 0.2 to 0.5, 1 or 2% w/w.

Where desired, more than one hydroxypyrone iron complex as described above may be present in the pharmaceutical composition or indeed other active compounds may be included in the composition, for example compounds having the ability to facilitate the treatment of anaemia, such as folic acid. Another additional component which may be included in the composition, if desired, is a source of zinc. Iron compounds used in the treatment of iron deficiency anaemia can inhibit the mechanism of zinc uptake in the body and this can cause serious side effects in the foetus when treating anaemia is in a pregnant female. It is believed, however, that the iron complexes of the present invention have a further advantage in that they either do not have this effect or exhibit the effect at a lower level than the compounds at present used in the treatment of anaemia. Accordingly, it may often be the case that the level of zinc providing compound added to the composition may not require to be high or, with preferred formulations of the iron complexes, may be dispersed with altogether.

Although certain of the iron complexes, for example iron maltol, have previously been proposed for use as colouring agents in foodstuffs, it had never previously been appreciated that they have any therapeutic use and the conditions proposed for the use of such complexes as colouring agents would not generally be such as to lead to any significant physiological effect. Accordingly the present invention includes an iron complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, for use in medicine, particularly in the treatment of iron deficiency anaemia.

We have found that the iron complexes described herein are particularly suited to the treatment of iron deficiency anaemia, both in humans and also in a veterinary context and particularly for the treatment of various mammalian species, especially pigs. Thus, the chelating agents which they contain, and particularly maltol, have a high affinity for iron (log $\beta_3 = 30$) for maltol) but a lower affinity for copper (II), zinc (II), calcium and magnesium. Both the high affinity of maltol for iron and its low affinity for calcium are reflected in its $K_{sol}$ value {log $K_{sol}$ is defined as being equal to log $\beta_{Fe(L)n} + 21 - [pK_{sp} + n \log a_{L(H+)} + m \log a_L(Ca++)]$ where log $\beta_{Fe(L)n}$ is the cumulative affinity constant of the ligand in question for iron (III), $pK_{sp}$ is the negative logarithm of the solubility product for $Fe(OH)_3$ and has a value of 39, n and m are the number of hydrogen and calcium ions, respectively, which are bound to the ligand, and $a_{L(H+)}$ and $a_L(Ca++)$ are the affinities of the ligand for hydrogen ions and calcium ions, respectively}. In order to solubilise iron (III) hydroxide, log $K_{sol}$ must be greater than 0. The value of $K_{sol}$ for maltol is 8.0 and this is also sufficiently large to prevent appreciable competition from phytate, phosphate, thiols and other potential ligands likely to occur in the intestinal lumen. In order to exchange iron efficiently with transferrin, the log $K_{sol}$ value should be close to that of apotransferrin, which is 6.0, so that maltol is also suitable in this respect. Moreover, although the neutral 3:1 maltol:iron (III) complex is thermodynamically stable (thermodynamic stability constant=30) it is also extremely labile and is therefore able to donate iron to high affinity sites, such as those found in apotransferrin. The half life for the exchange of iron (III) between the maltol complex and apotransferrin is 1 minute whereas, by contrast, the corresponding figure for the complex of EDTA with iron (III) is 4 days.

It will be appreciated, however, that in addition to possessing properties such as those described above for iron maltol, a compound which is to act as a source of iron through oral administration is required to to show a high level of membrane permeability. An indication of the properties of a compound in this respect is provided by the value of the partition coefficient ($K_{part}$) obtained on partition between n-octanol and Tris hydrochloride (20 mM, pH 7.4; Tris representing 2-amino-2-hydroxymethylpropane, 1,3-diol) at 20° C. and expressed as the ratio (concentration of compound in organic phase)/(concentration of compound in aqueous phase). The value of $K_{part}$ for the neutral 3:1 maltol:iron (III) complex is 0.5, which is well placed in the preferred range of 0.2 to 1.0 and compares favourably with the figures of 0.001 and 0.0015 for the EDTA:iron (III) complex and iron (III) ascorbate, respectively.

The value of the iron complexes of the present invention is confirmed by various in vitro and in vivo tests. Thus, their ability to permeate biological membranes is confirmed in practice by tests of the ability of the $^{59}Fe$ labelled iron complexes to permeate erythrocytes. Moreover, iron complexes of the present invention have been found to exhibit a high level of efficiency in promoting iron uptake, as measured in the rat small intestine, as compared with a range of other iron complexes currently marketed for the treatment of iron deficiency anaemia. In vivo experiments in the cat and rat have confirmed the value of iron maltol compounds as a source of iron, the iron uptake obtained either on intravenous administration or on direct administration into the small intestine being markedly superior to that obtained with commercially available iron compounds such as iron sulphate, iron EDTA and iron gluconate. It was found from these experiments that the iron was not excreted to any significant extent in the urine but became generally distributed throughout the body, the complexes donating iron to transferrin to an equilibrium level once they are present in the bloodstream.

Certain aspects of their formulation may enhance the activity of the complexes in particular contexts. Thus, although the neutral 3:1 ferric complexes are stable over a wide pH range from about 4 or 5 up to 10, they will dissociate at the pH values of less than 4 prevailing in the stomach to form a mixture of the 2:1 and 1:1 complex together with the free hydroxypyrone, and it has been found that the blood levels of $^{59}$Fe achieved on administration of the 3:1 complex into the small intestine are much higher than when administration is made into the stomach. However, when the stomach contents is flushed to the small intestine in in vivo cat experiments an increase of iron uptake occurs almost immediately. The undesirable effects of this dissociation on iron uptake may be countered by using one or more of the following procedures in the formulation of the iron complex. Firstly, one of several variations may be employed which avoid or reduce exposure of the iron complex to the acidic conditions of the stomach. Such approaches may range from a controlled release system, for example one based upon a polymer, which simply provides a delayed release of the complex, through a system which avoids dissociation under acidic conditions, for example by buffering, to a system which is pH sensitive and allows optimised release under alkaline conditions such as prevail in the small intestine. Specific examples of methods which may be used include the use of polymeric hydrogel formulations and liposome formulations.

A second approach to countering the effect of the acidic conditions prevailing in the stomach involves formulation of the complex in the pharmaceutical composition together with the metal-free hydroxypyrone from which it is derived. The dissociation of the neutral 3:1 ferric complex, for example, involves various equilibria between this complex, the 2:1 and 1:1 complexes, and the metal-free compound, so that the presence of the latter will inhibit this dissociation. Any proportion of the free compound can be advantageous in this context but little further advantage accrues from increasing the proportion beyond a certain level. A preferred range for the molar proportion of the free compound present in compositions according to the present invention is thus from 0 to 100 moles of free hydroxypyrone:1 mole of iron complex, particularly of the neutral 3:1 iron (III) complex. Conveniently, a proportion of up to no more than 20, 30 or 50 moles:1 mole is used with a lower level of 1 or 2 moles:1 mole, although to obtain a marked effect upon dissociation of the iron complex a proportion of at least 5 or 10 moles:1 mole is usually employed. Thus a preferred range is from 10 moles:1 mole to 20 moles:1 mole of metal-free hydroxy pyrone:iron complex. It will be appreciated that a mixture of the hydroxypyrone and iron complex in at least certain of the proportions described above is novel for the various hydroxypyrones, irrespective of the particular form of the iron complex, and that such novel mixtures are included by the present invention. The use of such a mixture is an important feature of the present invention since in principle it can enable one to obtain almost quantitative uptake of iron from the complex.

The use of an uncomplexed hydroxypyrone in admixture with its iron complex may also have another advantage in addition to the prevention of dissociation of the iron complex under acidic conditions. Thus, in certain pathological conditions there may be an excess of iron deposited at certain sites even though the patient exhibits an overall anaemia. In these patients the use of such a mixture has the advantage that the iron complex will remedy the overall anaemia whilst the free hydroxypyrone will act to remove iron from pathological to physiological sites. However, although it is preferable for the hydroxypyrone present in an iron donor to be rapidly metabolized in order that iron may be efficiently transferred to the binding proteins and eventually to the iron requiring mechanisms within the body, it is preferable for a hydroxypyrone being used as an iron remover not to be rapidly metabolized so that it remains in the system, taking up iron, for an extended period. Thus, for example, maltol is rapidly metabolized and is therefore particularly suited for use as an iron complex, but for this same reason it is not appropriate for use in the free form. It is also the case that different compounds may function more efficiently either in the free form as an iron remover or in complex form as an iron donor for quite other reasons. Accordingly the present invention includes a mixture of an iron complex of a 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms, together with a different 3-hydroxy-4-pyrone. Alternatively, the different 3-hydroxy-4-pyrone may be replaced by a quite different form of iron chelating agent. Examples of such other iron chelating agents which may be used include the substituted 3-hydroxypyrid-2-ones and -4-ones, and 1-hydroxypyrid-2-one and substituted 1-hydroxypyrid-2-ones (and salts of these various pyridones with a physiologically acceptable cation) described in co-pending U.S. patent application Ser. Nos. 592,271, 478,493, and 651,772.

When a free hydroxy-4-pyrone, hydroxypyrid-2-one, hydroxypyrid-4-one, or other iron chelating agent is present in admixture with the iron complex of a hydroxy-4-pyrone for the purpose of acting as an iron remover, then the amount of this agent used may be different than when a free hydroxypyrone necessarily corresponding to that present in the iron complex is present primarily to prevent dissociation. Thus the daily dosage of the iron complex may be as above and the daily dosage of the free iron chelating agent, particularly when this is a hydroxypyrid-2- or -4-one or a 1-hydroxypyrid-2-one, may be that quoted in the co-pending applications referred to above, i.e. about 0.1 g to 5 g for human use, particularly 0.5 g to 2 g, from which it will be seen that the proportion of iron complex and free iron chelating agent used in such a context may extend across a wide range but preferred amounts of the free iron chelating agent tend to be higher than when this is necessarily a hydroxypyrone.

It will be appreciated that the present invention also includes a method for the treatment of a human or other mammalian patient which comprises administering to said patient an iron complex of 3-hydroxy-4-pyrone or of a 3-hydroxy-4-pyrone in which one or more of the hydrogen atoms attached to ring carbon atoms are replaced by an aliphatic hydrocarbon group of 1 to 6 carbon atoms in order to effect an increase in the levels of iron in the patient's bloodstream.

In addition to the pharmaceutical uses of the iron complexes discussed above they are also of potential interest as a source of iron in various other contexts including cell and bacterial growth, plant growth, and the control of iron transport across membranes.

This invention is illustrated by the following Examples:

EXAMPLES

Example 1

The preparation of iron maltol

A chloroform solution of maltol is mixed with a 1M solution of ferric chloride in ethanol to provide a 3:1 molar ratio of maltol:iron in the mixture. After 5 minutes at 20° C., a 10 molar excess of solid sodium carbonate is added and the mixture is stirred for 10 minutes. The mixture is then filtered and the solvent evaporated to give the neutral complex containing maltol and the ferric cation in 3:1 proportion. Recrystallisation of the 3:1 complex from ethanol gives wine red needle crystals in an essentially quantitative yield, m.p. 275°, $v_{max}$ (nujol) 1600 cm$^{-1}$.

The use of an excess of maltol above the 3:1 molar ratio leads to an essentially quantitative yield of a solid mixture of the excess maltol and the 3:1 iron maltol complex on rotary evaporation, this mixture not being deliquescent.

The partition coefficient $K_{part}$ (concentration in n-octanol/concentration in aqueous phase) between n-octanol and Tris hydrochloride (20 mM, pH 7.4) of maltol and of its 3:1 iron complex is measured at $10^{-4}$M by spectrophotometry. Acid washed glassware is used throughout and, following mixing for 1 minute, the aqueous/n-octanol mixture is centrifuged at 1000 g for 30 seconds. The two resulting phases are separated for a concentration determination by spectrophotometry on each. For maltol, the range 220-340 nm is used for the concentration determination whilst for the complex the range 340-640 nm is used. Typically, a value of 0.66 is obtained for maltol and of 0.50 for its iron complex, whilst comparative experiments on iron (III) EDTA and iron (III) ascorbate give much smaller values of 0.001 and 0.0015, respectively.

The ability of the iron complex of maltol to bind to haemoglobin is investigated by studying the elution profile of a $^{59}$Fe label when a mixture of haemoglobin and the $^{59}$Fe-labelled complex (at 1 mM concentration) in NaCl (130 mM) buffered to pH 7.4 by Tris hydrochloride is applied to a PD-10 column (Sephadex G-10 gel permeation column—Pharmacia). Typically, no evidence is found for binding of the complex to haemoglobin which is an advantageous finding since such binding reduces availability of the iron.

The ability of the iron complex of maltol to bind to bovine serum albumen (BSA) is investigated through a similar procedure in which the complex also shows little ability to bind to BSA.

Example 2

In vitro tests on permeation of iron complexes into human erythrocytes

The accumulation of iron by human erythrocytes which are associated with the iron complex of maltol described in Example 1, and various other iron compounds by way of comparison, was studied by incubating the erythrocytes for 1 hour at 37° C. in a medium consisting of the $^{59}$Fe labelled iron compound in aqueous sodium chloride (130 mM) buffered to a pH of 7.4 by Tris hydrochloride. Following this period of incubation an aliquot of the erythrocyte/medium mixture was placed above a layer of silicone oil ($\rho = 1.06$) and the erythrocytes separated by centrifugation through the oil. The $^{59}$Fe levels associated with the erythrocytes and the incubation medium were then counted and presented as a distribution ratio (concentration in erythrocytes/concentration in medium). The ratios obtained for the various iron compounds after incubation for 1 hour are shown in Table 1 where it will be seen that the uptake of iron is clearly much greater with the iron maltol complex than with the other compounds. Values of less than 0.1 are probably associated with binding to the external surface and do not represent transmembrane movement of iron. Moreover, although a period of 1 hour was employed in order to facilitate monitoring of the more slowly permeating iron compounds, the uptake of the iron maltol complex reached equilibrium at the level shown after about 15 minutes.

TABLE 1

| Compound | Concentration (mM) | Distribution ratio |
|---|---|---|
| Fe$^{III}$ (maltol)$_3$ | 3 | 1.60 |
| Fe$^{II}$ gluconate | 1 | 0.08 |
| Fe$^{III}$ ascorbate | 1 | 0.12 |
| Fe$^{III}$ citrate | 1 | 0.05 |
| Fe$^{III}$ EDTA | 1 | 0.05 |

When the above described procedure was applied using ratios of maltol to iron of less than 3:1 larger apparent distribution ratios were observed than 1.60. However, this is explained by the non-specific binding of the positively charged 2:1 and 1:1 maltol:iron complexes to the surface of the erythrocytes which possesses a net negative charge, being rich in both phosphate and sulphate moieties. Experiments to determine the percentage of $^{59}$Fe associated with erthrocyte ghosts after lysis confirm this hypothesis. In one experiment, lysis was initiated by a small volume of 10% v/v Triton X100 and in a second experiment by a 10 fold excess of water. In each case the resulting ghosts were centrifuged through silicone oil ($\rho = 1.02$) and, as will be seen from Table 2, very little of the 3:1 maltol:iron complex was found to be bound to the membranes, in contrast with the situation with the 2:1 and 1:1 complexes. Such binding is of course undesirable as the complex is likely to remain tightly bound to the membrane by electrostatic interactions and not be transmitted across it.

TABLE 2

| Ratio of maltol:iron | Iron associatied with with ghosts (%) | |
|---|---|---|
| | Triton lysis | Hypotonic lysis |
| 0:1 | 100 | — |
| 1:1 | 55 | 63 |
| 2:1 | 22 | 39 |
| 3:1 | <1 | <5 |

Example 3

In vitro tests on permeation of rat jejunal sac by iron complexes

The iron uptake into the serosal space of the rat jejunal sac was compared for the iron complex of maltol described in Example 1 and various other iron compounds by way of comparison. Rats (male Sprague Dawley, 60 g) were killed and the jejunum removed, everted and cut into three segments (4 cm length). The segments were tied at both ends, filled with Krebs Ringer buffer (0.2 ml) and incubated in Krebs Ringer buffer containing the appropriate $^{59}$Fe compound at 37° C. for periods up to 90 minutes. The contents of the sac were counted for $^{59}$Fe and measured spectrophotometrically.

The results obtained for the iron maltol complex and for 6 other iron compounds which are each contained in preparations marketed for the treatment of iron deficiency anaemia are shown in Table 3, the iron uptake for each at 15 and 60 minutes after the initiation of the experiment being shown relative to that for ferric chloride as 1. It will be seen that the iron maltol complex provides a level of iron uptake which is significantly higher than the levels observed for any of the 6 compounds in current use for the treatment of iron deficiency anaemia. The uptake of the iron maltol complex was linear for a period of 90 minutes. Moreover, the uptake increased linearly as the concentration of the complex was increased over a range from 0.5 to 10 mM, so it does not show saturation kinetics and the process is thus non-facilitated and therefore should occur in all natural membranes.

TABLE 3

| Compound | Relative iron uptake | |
|---|---|---|
| | 15 minutes | 60 minutes |
| FeCl$_3$ | 1 | 1 |
| Fe$^{III}$(maltol)$_3$ | 40 | 5.8 |
| Fe$^{II}$ sulphate | 2.4 | 1.4 |
| Fe$^{II}$ fumarate | 4.0 | 1.8 |
| Fe$^{II}$ gluconate | 1.6 | 0.8 |
| Fe$^{II}$ succinate | 2.0 | 1.0 |
| Fe$^{III}$ ascorbate | 0.4 | 0.8 |
| Fe$^{III}$ citrate | 2.0 | 1.8 |

The procedure described above was used to compare the uptake of iron from buffer containing differing molar preparations of maltol:iron. The results obtained are presented in Table 4 which shows the amount of iron transferred via the maltol complex into the serosal contents of the sac, the basal uptake of iron measured in a control experiment being subtracted in each case. It will be seen that the amount of iron transferred in the case of a 3:1 molar preparation of maltol:iron (III) is much higher than in the other two cases and, moreover the low, but significant level of iron uptake observed in the case of a 2:1 ratio is attributed to the proportion of the 3:1 complex (containing 13% of the total iron) present under these conditions.

TABLE 4

| Maltol/iron (molar ratio) | Iron uptake (n mole) |
|---|---|
| 1:1 | 1.6 |
| 2:1 | 4.0 |
| 3:1 | 30.0 |

Example 4

In vivo test of action of iron compounds in the rat

The action of the iron complex of maltol described in Example 1 was compared with that of iron (I) sulphate, iron (III) EDTA (1:1 molar ratio) and iron (II) gluconate.

Groups of rats (300-350 g) were anaesthetised with nembutal (0.25 ml) and then with ether. A mid-line incision was made and the $^{59}$Fe labelled sample (100 μg Fe, 10 μCi) was passed into the lumen of the duodenum via a small incision. The abdominal well was then closed with a suture. The animals were sacrificed 1, 2, 4 and 6 hours after the administration of the compound and the various organs were monitored for their $^{59}$Fe content. The data is presented as histograms in FIGS. 1 to 4 which relate to iron maltol, iron sulphate, iron EDTA and iron gluconate, respectively, and show the levels of $^{59}$Fe in cpm after various time intervals for the different organs, the data in each case representing a mean of the results for three individual animals. In the case of the data for blood and sternum (bone marrow) the counts given are cpm/ml and cpm/g respectively, whilst in all other cases they are the total cpm counts. The various histograms have been normalised and consequently are directly comparable.

Figure 2:
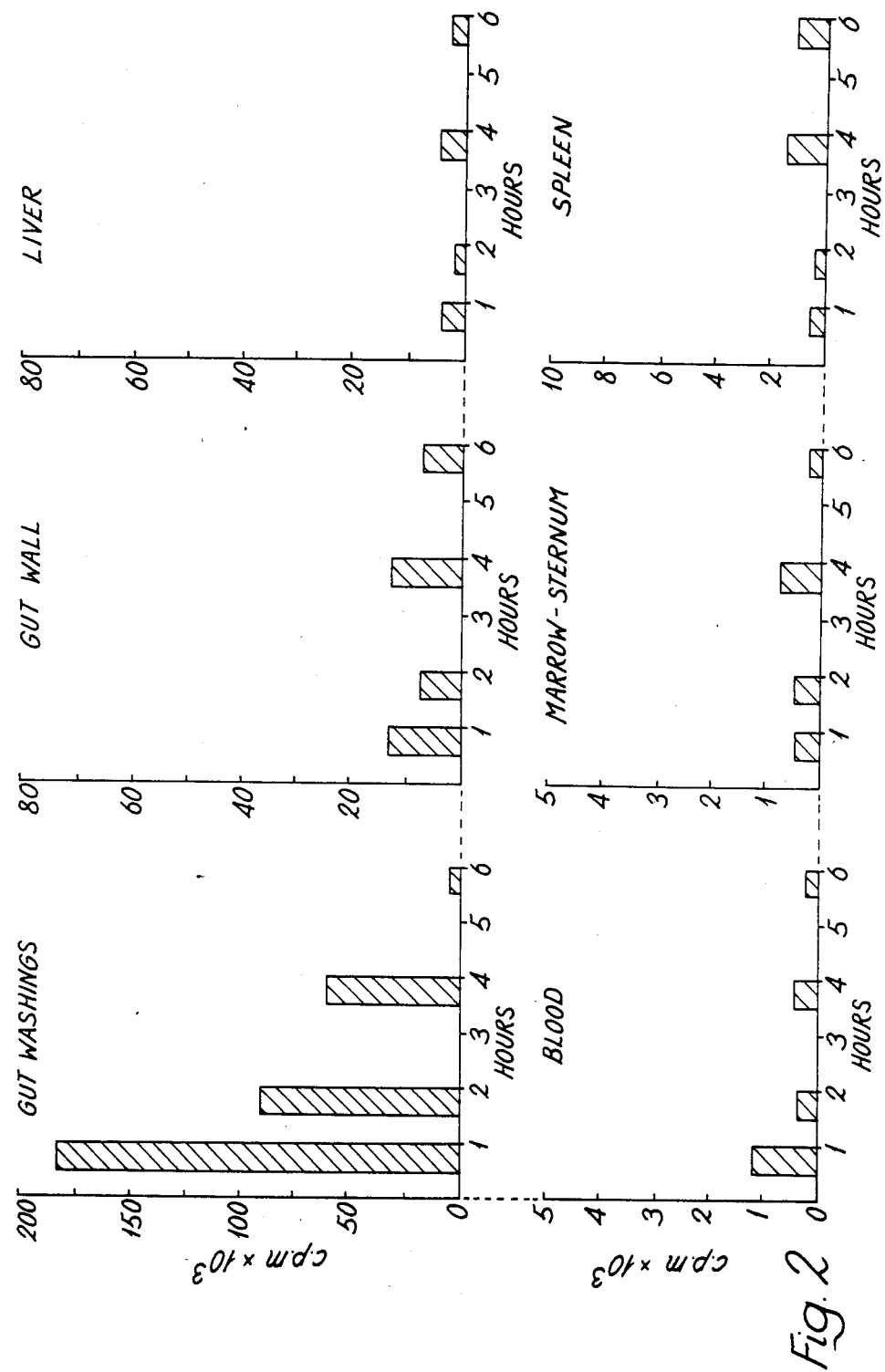

A comparison between FIGS. 1 and 2 shows that the neutral 3:1 maltol:iron (III) complex is markedly superior to iron (II) sulphate for the introduction of iron via the rat intestine. The gut washings (which contain non-absorbed iron) show a much lower level of counts for the maltol complex, and the counts associated with the gut wall, liver, blood, bone marrow and spleen are correspondingly greater. It is clear from FIG. 1 that $^{59}$Fe associated with maltol enters the intestine wall very rapidly and from there it is efficiently removed by the blood supply. Iron is deposited in the bone marrow continuously throughout the 6 hour period at an apparently constant rate.

Figure 3:
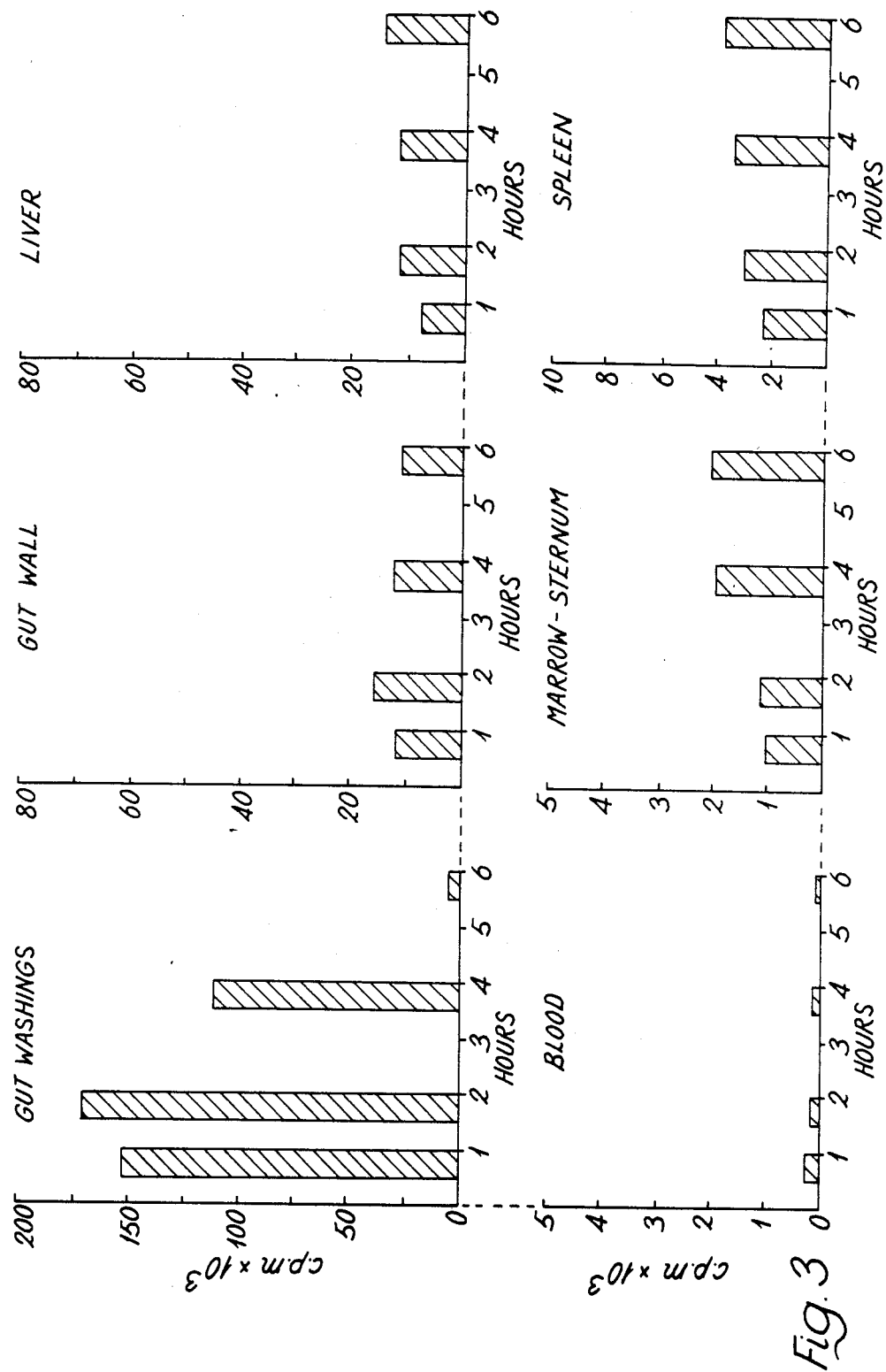
Figure 4:
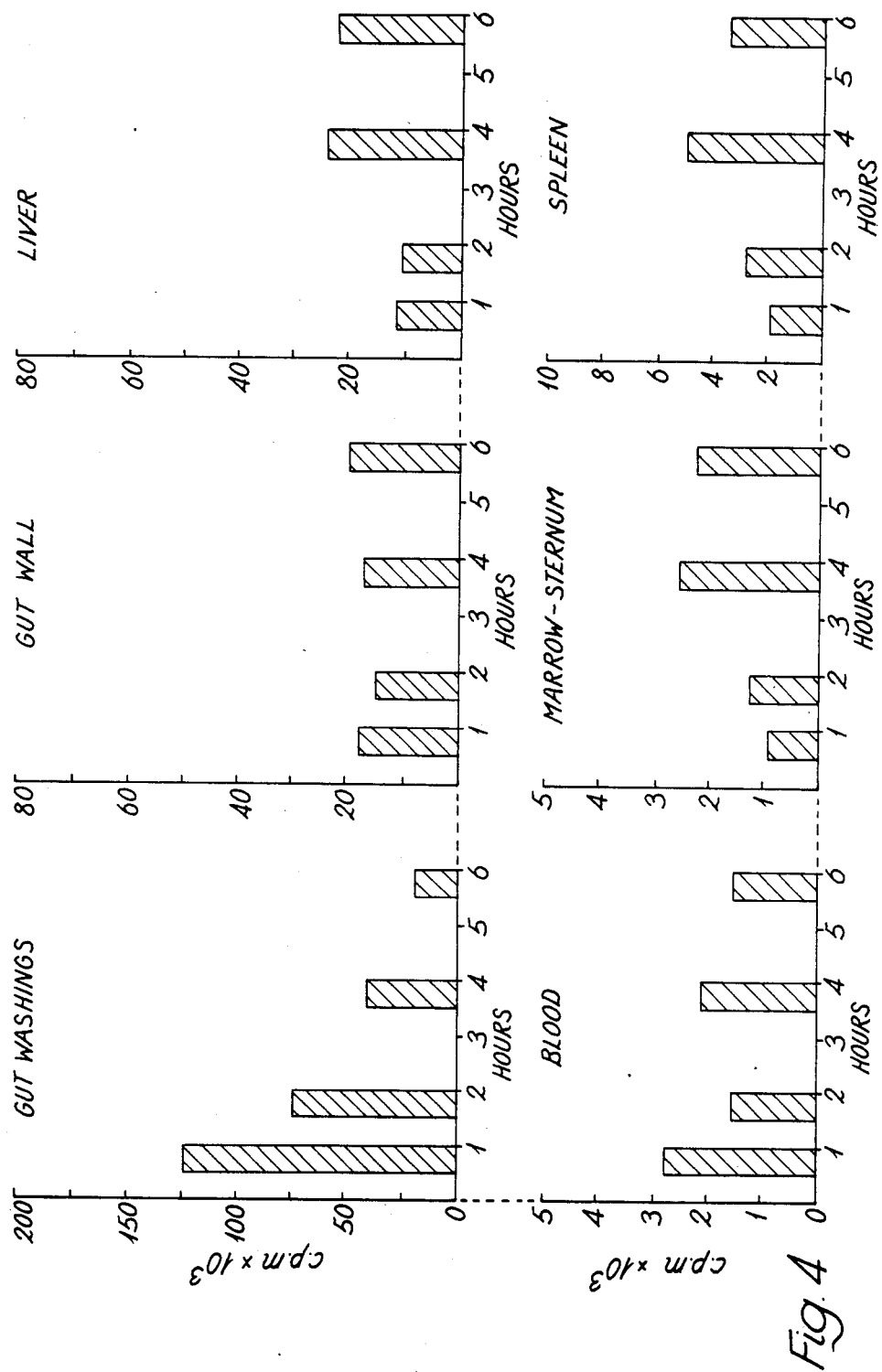

The maltol complex is also more efficient than iron (III) EDTA as shown by FIG. 3. With the later complex, the gut washings remain high for 4 hours and may be presumed to decrease only due to the effect of natural bowel movements translocating material from the portion under investigation to lower portions of the intestine. The levels in the intestine wall and blood are extremely low. Although iron is transferred to both bone marrow and spleen, this is at reduced rates as compared to those obtained with the maltol complex. As shown by FIG. 4, iron (II) gluconate proved more effective than the sulphate or the EDTA complex, although deposition in the gut wall was less than that observed with the maltol complex. The decrease was reflected in the lower levels of $^{59}$Fe in both bone marrow and the spleen, the difference being particularly marked after 6 hours. In view of the much higher levels of $^{59}$Fe trapped in the intestine wall in the case of the maltol complex, it may be predicted that this compound facilitates a more prolonged supply of iron than iron (II) gluconate.

This test illustrates the superiority of the neutral 3:1 maltol:iron (III) complex as compared with three commonly used "soluble iron" preparations for the movement of iron across the rat jejunal wall into the blood circulation, the iron maltol being very rapidly removed from the lumen of the intestine.

Example 5

In vivo test of action of iron complexes in the cat

The action of the iron complex of maltol described in Example 1 was compared with that of iron (III) EDTA (1:1 molar ratio) which is one of the iron compounds currently marketed for the treatment of iron deficiency anaemia. Cats were anaesthetised with chloralase (60 mg/kg) and pentabarbitone sodium (60 mg/kg) (i.p.), having been kept free of food for 18 hours. In each animal the trachea was cannulated to maintain a clear airway and to allow positive pressure artificial respiration if necessary. The left femoral vien was cannulated for the intravenous administration of drugs and physiological saline solution. Arterial blood pressure was monitored by a Washington pressure transducer through a cannula inserted into the femoral artery of the right hind leg. Arterial blood samples were taken at appropriate intervals from a short cannula inserted into an external carotid artery. Body temperature was monitored with a rectal thermometer. Each animal was given heparin (1000 iu/kg) as anticoagulant and additional small amounts of pentabarbitone sodium if needed to maintain a satisfactory level of anaesthesia.

In those animals where the iron compounds were to be administered into the duodenum, a mid-line incision was made in the abdomen to reveal the intestines. A cannula was then inserted through a small cut such that its tip rested approximately 5 cm below the opening of the bile duct. The cannula was then sutured in place and the abdominal wall closed with stitches.

The iron maltol complex (100 μg Fe) alone (3:1 molar ratio of maltol:iron) and together with a large excess of maltol (40:1 molar ratio of maltol:iron) was injected intravenously in separate experiments and 0.25 ml samples of blood were taken at intervals. The apparent volume of distribution of the compound was calculated by extrapolation of the log-linear blood concentration curve to zero. (The volume corresponds to a value between that of the total extracellular space of the animal and the blood volume.) Elimination of $^{59}$Fe from the blood followed first order kinetics with a rate constant of $-0.022$/minute in the presence and absence of excess maltol, as illustrated in FIG. 5 which shows the $^{59}$Fe level in the blood in cpm/0.25 ml plotted against time in the case of one typical experiment of each type in an individual cat.

Figure 5:
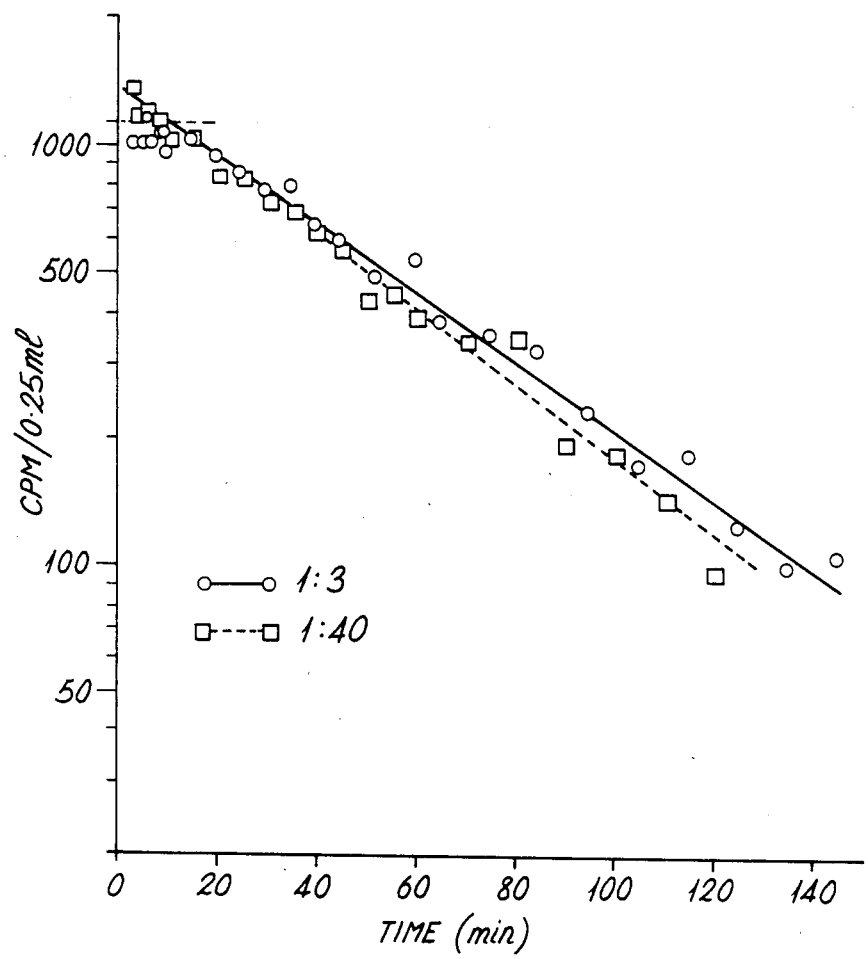

The distribution of $^{59}$Fe in the tissues of the animal after the same intravenous experiment to which FIG. 5 relates (the lower end of the ordinate in this Figure represents the background level) was investigated and the typical results are shown in Table 5. The amount of $^{59}$Fe administered in this experiment was 4 μCi or $2.2 \times 10^6$ cpm. It will be seen that approximately 10% of the dose was located in the combined tissue of the heart, liver and spleen. As less than 0.2% of the dose was located in the urine, the bulk (approximately 90%) of the $^{59}$Fe was almost certainly directed to the bone marrow and extremely high levels were found to be located in the sternum.

As indicated previously, the maltol complex is able to donate iron rapidly to transferrin and it is hypothesised that such an exchange occurs as soon as the complex is delivered to the plasma; and that the initial plateau (represented in FIG. 5 by a dotted line) represents saturation of the plasma transferrin pool with $^{59}$Fe. When there is net donation of $^{59}$iron from the plasma into the organs of the animal, the blood levels of radioactivity begin to fall, the major route of transfer of iron bound to transferrin being to the bond marrow, liver and spleen. Binding of $^{59}$Fe to transferrin prevents its excretion in the urine.

TABLE 5

| (Iron maltol, i.v.) | | | |
|---|---|---|---|
| Tissue | Total tissue weight (g) | Sample weight (g) | Net $^{59}$Fe content (cpm/g) | Net total $^{59}$Fe content (cpm) |
| Heart | 14.4 | 0.91 | 490 | 7,056 |

TABLE 5-continued

| (Iron maltol, i.v.) | | | |
|---|---|---|---|
| Tissue | Total tissue weight (g) | Sample weight (g) | Net $^{59}$Fe content (cpm/g) | Net total $^{59}$Fe content (cpm) |
| Liver | 105 | 1.3 | 510 | 53,550 |
| Spleen | 8.4 | 0.86 | 14,890 | 125,076 |
| Kidney | 12.2 | 1.05 | 546 | 6,661 |
| Skeletal muscle | — | 1.85 | 0 | 0 |
| Sternum (bone marrow) | — | 1.2 | 3,200 | — |
| Urine | — | 1 | 152 | <3,000 |

Figure 6:
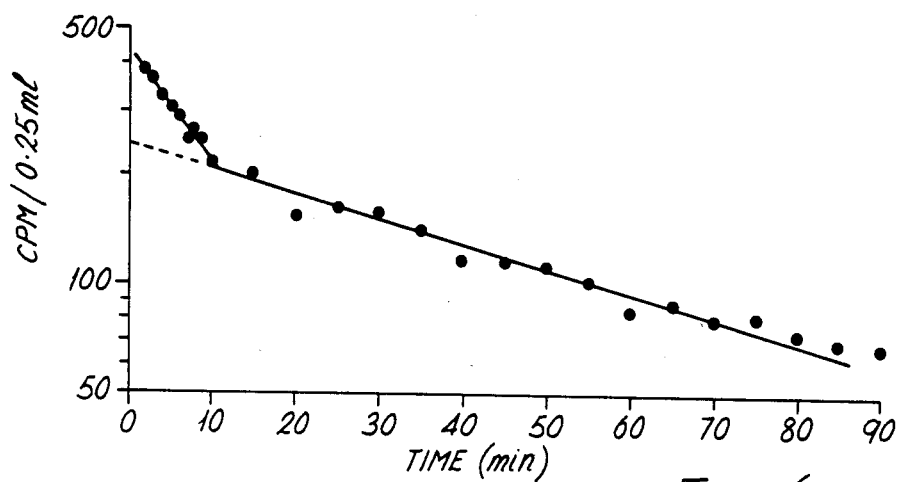

Identical experiments carried out with $^{59}$Fe labelled iron (III) EDTA gave a entirely different picture as will be seen for the results of a typical experiment illustrated in FIG. 6 (in which the lower end of the ordinate represents the background level) and Table 6 (the amount of $^{59}$Fe administered in this experiment was 2 μCi but the figures given in the table have been adjusted to correspond to a dosage of $2.2 \times 10^6$ cpm in order to facilitate comparison with Table 5). In this experiment the radioactivity in the blood showed no initial plateau. Instead, loss of radioactivity followed at least a two-component process such that a large amount found its way to the urine rather than to the tissues. The rate constant of the elimination from the blood of the linear phase of the regression was 0.023/minute. The concentration of radioactivity in the kidney and urine, and not in the bone marrow or spleen, would indicate that iron in this form does not appear to be able to attach to transferrin in the plasma and protect itself from urinary excretion. The combined tissue of heart, liver and spleen contained only 1% of the original dose at the end of the experiment, whereas the urine contained over 50%. This is in accord with the fact that EDTA does not exchange iron with transferrin rapidly.

TABLE 6

| (Iron EDTA, i.v.) | | | |
|---|---|---|---|
| Tissue | Total tissue weight (g) | Sample weight (g) | Net $^{59}$Fe content (cpm/g) | Net total $^{59}$Fe content (cpm) |
| Heart | 15.5 | 1.01 | 209 | 3,248 |
| Liver | 75 | 1.21 | 261 | 19,600 |
| Sternum (bone marrow) | — | 0.28 | 1,164 | — |
| Spleen | 11.2 | 0.89 | 162 | 1,814 |
| Kidney | 19.2 | 1.47 | 1,134 | 21,770 |
| Skeletal muscle | — | 2.59 | 95 | — |
| Urine | 19 ml | 2 ml | 62,156 | 1,180,900 |

Figure 7:
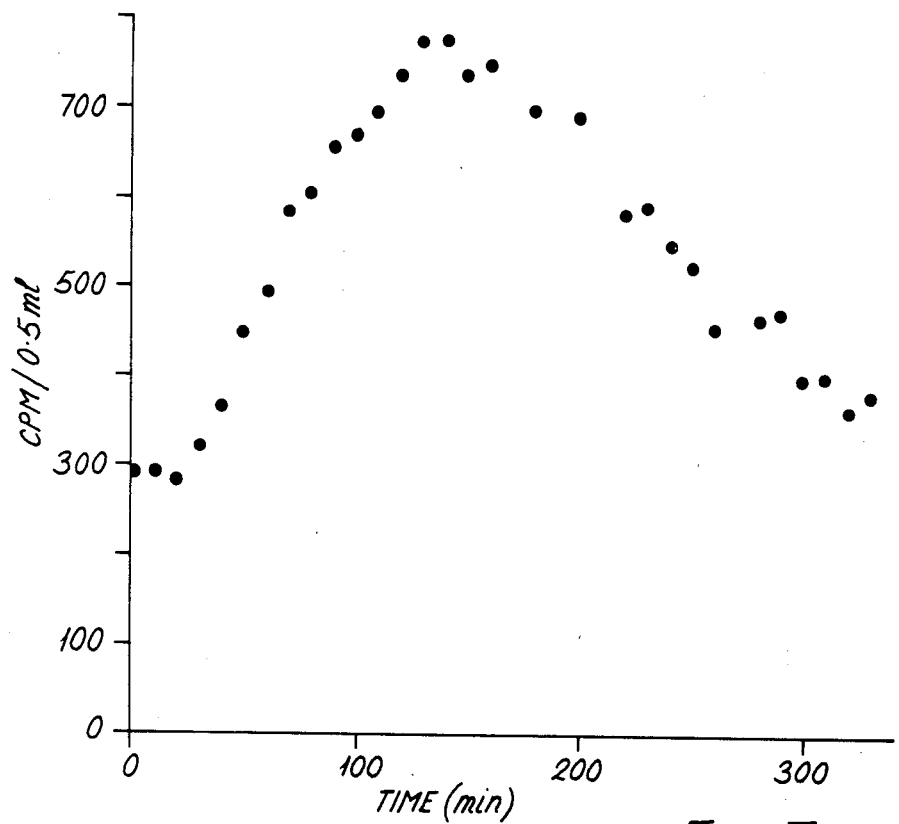

The iron maltol complex (100 μg Fe) was also administered to the duodenum of the cat in the presence of a 40 fold excess of maltol followed by 5 ml of 150 ml Tris hydrochloride buffer (pH 7.4). In this case the $^{59}$Fe content of the blood, as shown in FIG. 7, reaches a maximum level 2 hours after the initial administration (the readings start at about 300 cpm/0.5 ml which represents the background reading). The distribution of $^{59}$Fe in the tissues of the animal after the same duodenal experiment to which FIG. 7 relates were investigated and the typical results are shown in Table 7. The amount of $^{59}$Fe administered in this experiment was 10 μCi or $5.327 \times 10^6$ cpm into a 2.9 kg cat. It will be seen that the distribution of the $^{59}$Fe after 4 hours was similar to that after intravenous infusion, with low levels in the kidney and urine and high levels in both the spleen and bone marrow.

TABLE 7

(Iron maltol, per duodenum)

| Tissue | Total tissue weight (g) | Sample weight (g) | Net $^{59}$Fe content (cpm/g) | Net total $^{59}$Fe content (cpm) |
|---|---|---|---|---|
| Heart | 14 | 0.633 | 50 | 1,106 |
| Liver | 81 | 1.45 | 400 | 32,400 |
| Spleen | 12.7 | 1.19 | 3,783 | 48,047 |
| Kidney | 14.4 | 0.835 | 79 | 1,138 |
| Sternum (bone marrow) | 10 | 1.26 | 790 | 7,905 |
| Bile | ~5 ml | 1 ml | 2,200 | ~11,000 |
| Urine | ~10 ml | 1 ml | 22 | ~220 |

When $^{59}$Fe labelled iron (III) EDTA was administered duodenally in the same manner, the plasma levels of radioactivity hardly exceeded the background level and are therefore not illustrated in a Figure. The distribution of $^{59}$Fe in the tissues of the animal after the same duodenal experiment were investigated and the typical results are shown in Table 8. The amount of $^{59}$Fe administered in this experiment was 10 μCi or $2.65 \times 10^6$ cpm into a 2.9 kg cat. It will be seen that, although some $^{59}$Fe entered the tissues, rather low levels were detected in the spleen and bone marrow (sternum) whereas a large proportion of the dose was located in the urine.

TABLE 8

(Iron EDTA, per duodenum)

| Tissue | Total tissue weight (g) | Sample weight (g) | Net $^{59}$Fe content (cpm/g) | Net total $^{59}$Fe content (cpm) |
|---|---|---|---|---|
| Heart | 15.3 | 1.18 | 188 | 2,878 |
| Liver | 59.3 | 0.78 | 499 | 29,574 |
| Kidney | 11.3 | 0.90 | 1,762 | 19,913 |
| Spleen | 4.4 | 0.42 | 200 | 880 |
| Sternum (bone marrow) | — | 0.78 | 917 | — |
| Skeletal muscle | — | 1.48 | 117 | — |
| Urine | ~15 ml | 5 ml | 36,306 | 544,596 |

Example 6

Polymer formulation of iron maltol

A solution of ferric chloride (concentration between 1 and 5% v/v), together with maltol in a weight ratio of 8 parts by weight of maltol to 1 part by weight of ferric chloride, is prepared in a 4.5:4.5:1 v/v/v mixture of chloroform:methanol:water. Sodium carbonate is added in a 10 molar excess over the iron content in order to remove hydrochloric acid and the precipitated NaCl and Na$_2$CO$_3$ are filtered off. The preparation is contacted with a cross-linked polyethylene glycol hydrogel material to effect take up of the solution by the polymer and provide a polymer formulation of iron maltol in the presence of excess maltol.

We claim:

1. A method for the treatment of a patient to effect an increase in the level of iron in the patient's bloodstream, which comprises:
    administering to said patient in need thereof a compound comprising a tissue permeable, neutral iron complex of 3-hydroxy-4-pyrone or of a 3-hydroxy-4-pyrone in which at least one of the hydrogen atoms attached to ring carbon atoms is replaced by an aliphatic hydrocarbon group of 1 to 6 carbon atoms, in an amount which is effective to achieve such an increase, said iron complex being a 3:1 hydroxypyrone:iron (III) complex.

2. A method according to claim 1, in which each aliphatic hydrocarbon group is an acyclic group of 1 to 4 carbon atoms.

3. A method according to claim 1, in which each aliphatic hydrocarbon group is an alkyl group.

4. A method according to claim 1, in which the compound is an iron complex of a 3-hydroxy-4-pyrone in which at least one of the hydrogen atoms attached to ring carbon atoms is replaced by the same or different substituents selected from the group consisting of methyl, ethyl, n-propyl and isopropyl.

5. A method according to claim 4, in which each substituent is a methyl group.

6. A method according to claim 4, in which the substituted 3-hydroxy-4-pyrone has a single substituent at the 2- or 6-position.

7. A method according to claim 1, in which the compound is an iron complex of 3-hydroxy-4-pyrone, 3-hydroxy-2-methyl-4-pyrone, 3-hydroxy-6-methyl-4-pyrone or 2-ethyl-3-hydroxy-4-pyrone.

8. A method according to claim 1, in which the compound is an iron complex of 3-hydroxy-2-methyl-4-pyrone.

9. A method according to claim 1, in which the neutral 3:1 complex is substantially free from complexes containing other proportions of the hydroxypyrone and iron.

10. A method according to claim 1, in which the iron complex is in substantially pure form.

11. A method according to claim 1, in which the compound is an iron complex of 2-ethyl-3-hydroxy-4-pyrone.

12. A method according to claim 1, wherein said iron complex is administered to said patient together with an iron chelating agent.

13. A method according to claim 12, wherein said iron chelating agent is the same hydroxypyrone as in said iron (III) complex, or a salt thereof containing a physiologically acceptable cation, in uncomplexed form.

* * * * *